United States Patent
Maltz et al.

(10) Patent No.: US 8,666,472 B2
(45) Date of Patent: Mar. 4, 2014

(54) ARTERIAL ENDOTHELIAL FUNCTION MEASUREMENT METHOD AND APPARATUS

(75) Inventors: Jonathan S. Maltz, Oakland, CA (US); Thomas F. Budinger, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1505 days.

(21) Appl. No.: 11/362,326

(22) Filed: Feb. 23, 2006

(65) Prior Publication Data

US 2006/0264755 A1  Nov. 23, 2006

Related U.S. Application Data

(63) Continuation of application No. PCT/US2004/029737, filed on Sep. 10, 2004.

(60) Provisional application No. 60/502,766, filed on Sep. 12, 2003.

(51) Int. Cl.
*A61B 5/02* (2006.01)

(52) U.S. Cl.
USPC .................................. 600/407; 600/437

(58) Field of Classification Search
USPC ......... 600/300, 437, 438, 449, 450, 454, 455, 600/485, 500–504
See application file for complete search history.

(56) References Cited

U.S. PATENT DOCUMENTS

| 3,095,872 | A | * | 7/1963 | Tolles | 600/485 |
| 3,897,790 | A | * | 8/1975 | Magilton et al. | 607/105 |
| 5,033,472 | A | | 7/1991 | Sato et al. | |
| 5,680,870 | A | | 10/1997 | Hood, Jr. et al. | |
| 5,797,850 | A | * | 8/1998 | Archibald et al. | 600/494 |
| 5,848,970 | A | | 12/1998 | Voss et al. | |
| 6,152,881 | A | | 11/2000 | Rines et al. | |
| 6,200,270 | B1 | | 3/2001 | Biehl et al. | |
| 6,228,034 | B1 | | 5/2001 | Voss et al. | |

(Continued)

OTHER PUBLICATIONS

Andrews et al., "Effect of Gemfibrozil +/− Niacin +/− Cholestyramine on Endothelial Function in Patients With Serum Low-Density Lipoprotein Cholesterol Levels <160 mg/dl and High-Density Lipoprotein Cholesterol Levels <40 mg/dl", The American Journal of Cardiology, vol. 80, p. 831-835, (Oct. 1997).

(Continued)

*Primary Examiner* — Tse Chen
*Assistant Examiner* — Mark Remaly
(74) *Attorney, Agent, or Firm* — Michelle Chew Wong; Lawrence Berkeley National Laboratory (57) ABSTRACT

A "relaxoscope" (100) detects the degree of arterial endothelial function. Impairment of arterial endothelial function is an early event in atherosclerosis and correlates with the major risk factors for cardiovascular disease. An artery (115), such as the brachial artery (BA) is measured for diameter before and after several minutes of either vasoconstriction or vasorelaxation. The change in arterial diameter is a measure of flow-mediated vasomodification (FMVM). The relaxoscope induces an artificial pulse (128) at a superficial radial artery (115) via a linear actuator (120). An ultrasonic Doppler stethoscope (130) detects this pulse 10-20 cm proximal to the point of pulse induction (125). The delay between pulse application and detection provides the pulse transit time (PTT). By measuring PTT before (160) and after arterial diameter change (170), FMVM may be measured based on the changes in PTT caused by changes in vessel caliber, smooth muscle tone and wall thickness.

10 Claims, 6 Drawing Sheets

(56) References Cited

U.S. PATENT DOCUMENTS

| | | | |
|---|---|---|---|
| 6,322,515 B1 | 11/2001 | Goor et al. | |
| 6,338,719 B1 | 1/2002 | Drzewiecki et al. | |
| 6,364,842 B1 | 4/2002 | Amano et al. | |
| 6,398,734 B1 | 6/2002 | Cimochowski et al. | |
| 6,592,520 B1 | 7/2003 | Peszynski et al. | |
| 6,626,840 B2 | 9/2003 | Drzewiecki et al. | |
| 6,908,436 B2 | 6/2005 | Chowienczyk et al. | |
| 2001/0016690 A1* | 8/2001 | Chio | 600/485 |

OTHER PUBLICATIONS

Anliker et al., "Dispersion and Attenuation of Small Artificial Pressure Waves in the Canine Aorta", Circulation Research, vol. 23, p. 539-551, (Oct. 1968).

Celermajer et al., "Endothelium-dependent Dilation in the Systemic Arteries of Asymptomatic Subjects Relates to Coronary Risk Factors and their Interaction", Journal of the American College of Cardiology, vol. 24, p. 1468-1474, (Nov. 1994).

Celermajer et al., "Non-invasive Detection of Endothelial Dysfunction in Children and Adults at Risk of Atherosclerosis", The Lancet, vol. 340 (No. 8828), (Nov. 7, 1992).

Cox et al., "Atherosclerosis Impairs Flow-Mediated Dilation of Coronary Arteries in Humans", Circulation, vol. 80, p. 458-465, (Sep. 1989).

De Roos et al., "Replacement of Dietary Saturated Fatty Acids by Trans Fatty Acids Lowers Serum HDL Cholesterol and Impairs Endothelial Function in Healthy Men and Women", Arteriosclerosis, Thrombosis, and Vascular Biology, vol. 21, p. 1233-1237, (2001).

Dinnar, Cardiovascular Fluid Dynamics, CRC Press: Boca Raton, Fla., p. 91, (1981).

Hardie et al., "Reproducibility of Brachial Ultrasonography and Flow-Mediated Dilation (FMD) for Assessing Endothelial Function", Australian and New Zealand Journal of Medicine, vol. 27, p.649-652, (Dec. 1997).

Higashi et al., "Regular Aerobic Exercise Augments Endothelium-Dependent Vascular Relaxation in Normotensive as Well as Hypertensive Subjects: Role of Endothelium-Derived Nitric Oxide", Circulation, vol. 100, p. 1194-1202, (Sep. 1999).

Krauss et al., "AHA Dietary Guidelines: Revision 2000: A Statement for Healthcare Professionals From the Nutrition Committee of the American Heart Association", Circulation, vol. 102, p. 2284-2299, (Oct. 2000).

Landowne, "A Method Using Induced Waves to Study Pressure Propagation in Human Arteries", Circulation Research, vol. 5, p. 594-601, (Nov. 1957).

Löfberg et al., "The Role of Duplex Scanning in the Selection of Patients with Critical Lower-Limb Ischemia for Infrainguinal Percutaneous Transluminal Angioplasty", Cardiovascular and Interventonal Radiology, vol. 24, p. 229-232, (May 17, 2001).

Loukogeorgakis et al., "Validation of a Device to Measure Arterial Pulse Wave Velocity by a Photoplethysmographic Method", Physiological Measurement, vol. 23, p. 581-596, (Aug. 2002).

Maltz et al., "Instrument for the Non-invasive Evaluation of Human Arterial Endothelial Function via Measurement of Changes in the Transmit time of an Artificial Pulse", Proceedings of the 25th Annual International Conference of the IEEE, vol. 4, p. 3133-3136, (Sep. 2003).

McLenachan et al., "Early Evidence of Endothelial Vasodilator Dysfunction at Coronary Branch Points", Circulation, vol. 82, p. 1169-1173, (1990).

Neunteufl et al., "Late Prognostic Value of Flow-Mediated Dilation in the Brachial Artery of Patients with Chest Pain", The American Journal of Cardiology, vol. 86, p. 207-210, (Jul. 15, 2000).

Nichols et al., McDonald's Blood Flow in Arteries, 4th Ed., Edward Arnold: London, p. 100-106, (1998).

Ross, "The Pathogenesis of Atherosclerosis: A Perspective for the 1990s", Nature, vol. 362, p. 801-809, (Apr. 29, 1993).

Sorensen et al., "Impairment of Endothelium-dependent Dilation is an Early Event in Children with Familial Hypercholesterolemia and is Related to the Lipoprotein (a) Level", Journal of Clinical Investigation, vol.92, p. 50-55, (Jan. 1994).

Sorensen et al., "Non-invasive Measurement of Human Endothelium Dependent Arterial Responses: Accuracy and Reproducibility", British Heart Journal, vol. 74, p. 247-253, (Sep. 1995).

Vita et al., "Coronary Vasomotor Response to Acetylcholine Relates to Risk Factors for Coronary Artery Disease", Circulation, vol. 81, p. 491-497, (1990).

Williams et al., "Impaired Endothelial Function Following a Meal Rich in Used Cooking Fat", Journal of the Americal College of Cardiology, vol. 33, p. 1050-1055, (Mar. 1999).

Wolf et al., "Duplex Ultrasound Scanning Versus Computed Tomographic Angiography for Postoperative Evaluation of Endovascular Abdominal Aortic Aneurysm Repair", Journal of Vascular Surgery, vol. 32 (No. 6), p. 1142-1148, (Dec. 2000).

Yasue et al., "Responses of Angiographically Normal Human Coronary Arteries to Intracoronary Injection of Acetylcholine by Age and Segment. Possible Role of Early Coronary Atherosclerosis", Circulation, vol. 81, p. 482-490, (1990).

Zeiher et al., "Modulation of Coronary Vasomotor Tone in Humans. Progressive Endothelial Dysfunction with Different Early Stages of Coronary Atherosclerosis", Circulation, vol. 83, p. 391-401, (1991).

* cited by examiner

ARTERIAL ENDOTHELIAL FUNCTION MEASUREMENT METHOD AND APPARATUS

CROSS REFERENCE TO RELATED APPLICATIONS

This application claims priority to and is a continuation of international patent application PCT/US2004/029737 filed Sep. 10, 2004, which in turn claims priority to U.S. provisional patent application 60/502,766, entitled "Arterial Endothelial Function Measurement Method and Apparatus", filed Sep. 12, 2003, both of which are hereby incorporated by reference in their entireties.

STATEMENT REGARDING FEDERAL FUNDING

This invention was made with U.S. Government support under Contract Number DE-AC02-05CH11231 between the U.S. Department of Energy and The Regents of the University of California for the management and operation of the Lawrence Berkeley National Laboratory. The U.S. Government has certain rights in this invention.

REFERENCE TO A COMPUTER PROGRAM

Not applicable.

BACKGROUND OF THE INVENTION

1. Field of the Invention

The present invention pertains generally to methods and apparatus used in evaluation of cardiovascular health, and more particularly to the evaluation of cardiovascular health by techniques of arterial endothelial function measurement by vasorelaxation or vasoconstriction.

2. Description of the Relevant Art

Most measurements of arterial endothelial function are limited to researchers due to the cost of such measurements. Typically, such measurements have low reliability, and need further improvement before an average physician would recommend arterial endothelial function tests for the detection of symptoms indicative of extremely early stage atherosclerosis. Presently, arterial endothelial function tests are done by ultrasound imaging using the same devices already commercially available for internal organ imaging. Such devices are ill disposed to maintain constant skin contact and precisely image arteries.

Voss et al. U.S. Pat. No. 5,848,970 (the '970 patent), hereby incorporated by reference, discloses an apparatus for non-invasively monitoring a subject's blood pressure. In the '970 patent, a flexible diaphragm enclosing a fluid-filled chamber is compressed against the tissue overlying an artery with sufficient force to compress the artery. However, the invention described herein measures endothelial function by the calculation of arterial elasticity.

Voss et al., in U.S. Pat. No. 6,228,034 (the '034 patent), also hereby incorporated by reference, relates generally to apparatus and methods for monitoring a subject's arterial blood pressure and, more particularly, to such apparatus and methods that monitor arterial blood pressure non-invasively by applying a pressure sensor against tissue overlying an arterial blood vessel, to partially applanate or compress the vessel.

Sato et al. in U.S. Pat. No. 5,033,472, hereby incorporated by reference, provides a non-invasive method and apparatus for automatically analyzing the fluctuation and distribution of the propagation time of arterial pulse waves. Such method and apparatus are based upon a fact that the degree of fluctuation in the propagation time of the arterial pulse wave from the center of the circulatory system (i.e. heart) to the periphery of the circulatory system, can serve as a diagnostic index of vascular wall tensions or an indication of diseases through a statistical analysis of such propagation times. The invention described herein measures the pulse transit time in an artery from an artificially induced pulse to a sensor.

Biehl et al., in U.S. Pat. No. 6,200,270, attached hereto and incorporated by reference herein, provides a sensor for non-invasive and continuous determination of the duration of arterial pulse waves, but may not be successfully used to measure arterial endothelial function.

Similarly, Hood et al., in U.S. Pat. No. 5,680,870, attached hereto and incorporated by reference herein, provide an automated sphygmomanometer that measures static blood pressure, but not endothelial function.

Drzewiecki et al., U.S. Pat. No. 6,626,840, hereby incorporated by reference, describe an occlusive arm cuff plethysmograph to measure the flow of air, the pulse pressure waveform and the change in air volume in a blood vessel to measure arterial endothelial function. This is done by looking at pressure versus lumen area curves, which in turn provides information on the compliance and elasticity of the vessel. Drzewiecki et al. do not use pulse wave velocity and do not output a direct pulse wave velocity measurement. The method is dependent on uniform arterial dilation and calibration, limitations that the present invention does not have. Additionally, the present invention measures pulse wave velocity directly, and does not use an occlusive cuff plethysmograph.

Loukogeorgakis et al. in "Validation of a device to measure arterial pulse wave velocity by a photoplethysmographic (PPG) method" [Physiol. Meas. 23 (August 2002) 581-596] measure the pulse wave velocity from an echocardiograph (ECG) "R" wave by determining propagation velocity of the diameter wave of a vessel using an infra-red emitting diode probe and a phototransistor detector. They also compared Doppler ultrasound and the PPG method for measuring pulse wave delay (the time between the ECG "R" wave and the foot of the arterial pulse wave). In the present invention, an ultrasonic method of measuring pulse wave velocity is used. Additionally, a low-pressure artificial pulse is induced rather than the normally occurring arterial pulse. The present invention's low-pressure artificial pulse minimizes the non-linear response region of the elastic properties of the arterial wall, which occurs during somatic cardiac pulse propagation. The artificial pulse also has a more clearly defined rising edges than a somatic cardiac pulse, which greatly improves the timing accuracy and resolution for pulse transit times. Non-linear acoustic dispersive effects tend to blur these edges owing to dispersion of frequency components in the pulse spectrum.

BRIEF SUMMARY OF THE INVENTION

This invention provides for a method of arterial endothelial function measurement, the method comprising: a) imparting a first set of one or more pulses into an artery, said artery having an initial (or unmodified) pulse transit speed; b) detecting the arrival of at least one of said first set of pulses at a detector to form the initial (or unmodified) pulse transit speed; then c) modifying the pulse transit speed of said artery; then) imparting a second set of one or more pulses into said artery; and e) detecting the arrival of at least one of said second set of pulses with said detector to form a modified pulse transit speed.

The method may further comprise the step of: a) calculating a difference between said modified pulse transit speed and said initial (or unmodified) pulse transit speed. Alternatively, the method may further comprise calculating a ratio between said modified pulse transit speed and said initial pulse transit speed.

In general, the distance between the actuator imparting the pulses and the detector receiving the pulses will remain substantially the same distance, however, these distances could be changed by accounting for the change in distance between the pulse origin beneath the actuator, and the detector. By taking into account the changed distances, pulse transit speeds may be compared. Such speeds, taken over a standardized distance, would give standardized pulse transit times, and could again be used to detect arterial endothelial function.

The methods described above may further comprise the outputting of one or more signals based on the said change in said artery's interior diameter as a signal output and/or as a measurement output to a computer readable medium. Such signals may include one selected from the group: initial pulse transit speed, modified pulse transit speed, the difference of pulse transit speeds, and the ratio of pulse transit speeds. Since the actuator imparting the pulses that are subsequently measured is controlled by a computer or microprocessor, it is very easy to output the signals describing pulse transit times before and after vasomodification, the distance traveled, the percentage change in arterial diameter, and an estimation of the degree of health or risk associated with the individual level of arterial endothelial function when compared to pulse transit time correlations to physiological health.

Vasomodification may be accomplished either by constricting or by relaxing a surface artery. The radial artery, located in the forearm, is perhaps the most convenient locations to take this measurement for many purposes. When the vasomodification is induced by relaxation of the artery endothelial cells, several methods may be used to induce such relaxation, such as one or more of the group consisting of: electrostimulation (with waveforms causing relaxation), reactive hyperemia, applying vasorelaxant sodium nitroprusside, and applying vasorelaxants nitroglycerin, serotonin, methacholine, donepezil, carbon dioxide, nicotine, acetylcholine and beta-2 adrenergic agents such as albuterol and salbutamol that have been shown to directly stimulate endothelial receptors. A device based on the vasorelaxation may be referred to as a "relaxoscope", as used herein, although the same device may be equally well suited for operation using vasoconstriction test methods.

Where vasomodification is induced by vasoconstriction, the artery may be constricted by one or more of the group consisting of: electrostimulation (with waveforms causing stimulation), L-NAME, L-NMMA, nitric oxide synthase inhibitors, carbon dioxide, nicotine, epinephrine, and norepinephrine.

In one embodiment of the invention, pulse arrival is detected by a high frequency Doppler ultrasonic stethoscope, pulsed wave flow measurement device, or other ultrasonic imager, electromagnetic detector, optical detector, force sensor, microphone, and nuclear magnetic resonance imager. Pulses are typically imparted via a force-displacement controlled linear actuator.

The methods and apparatus described above may be integrated into an article of manufacture for arterial endothelial function measurement using a computer, said article could comprise: a computer readable medium comprising instructions for a computer to execute, said execution comprising the steps described above for measuring arterial endothelial function.

In yet another embodiment, a method is disclosed of determining arterial endothelial sensitivity to vasorelaxation or vasoconstriction, said method comprising: measuring changes in the pulse transit times in an artery before and after application of vasorelaxation or vasoconstriction. Alternatively, a method of determining arterial endothelial sensitivity to vasorelaxation or vasoconstriction, said method comprising: measuring changes in the time delay between a segment of the electrocardiogram waveform and a detected flow or pressure pulse in an artery before and after application of vasorelaxation or vasoconstriction.

In terms of a hardware implementation, an apparatus for arterial endothelial function measurement will typically comprise: a) an actuator to create one or more pulses in an artery; and b) a detector of said pulses in said artery; c) whereby said actuator creates one or more of said pulses in said artery, and said detector detects one or more of said pulses in said artery a distance away from said actuator. The pulses may be of any arbitrary waveform, and may be chirped to provide better pulse detection properties by taking into account the acoustic dispersion properties of an artery.

The actuator is typically a force-displacement controlled linear actuator, although it is possible that other devices having force-displacement curves of a similar nature may be built using purely mechanical and/or electromechanical devices. The actuator armature may be directly coupled to the skin using a shaft, a pneumatic, or a hydraulic system.

Typical distances between the source of the pulse and the point of detection could be as diverse as 1-50 cm. A more practical distance range would be 5-35 cm. In typical usage, it is most convenient to use a distance of 10-20 cm.

Unlike other methods using implanted actuators and/or detectors, this device uses an exogenous actuator and detector. The apparatus may also create a signal output of a pulse transit time, said pulse transit time the difference between actuation of said actuator to create said pulses, and said detector detecting said pulses. Alternatively, the apparatus may also comprise a signal output of a differential pulse transit time, said differential the difference between pulse transit time after vasomodification, and the pulse transit time prior to vasomodification.

BRIEF DESCRIPTION OF THE SEVERAL
VIEWS OF THE DRAWINGS

The invention will be more fully understood by reference to the following drawings, which are for illustrative purposes only.

DETAILED DESCRIPTION OF THE PREFERRED EMBODIMENT

Defined Terms

Computer means any device capable of performing the steps developed in this invention to result in an arterial endothelial function measurement, including but not limited to: a microprocessor, a microcontroller, a digital state machine, a field programmable gate array (FGPA), a digital signal processor, a collocated integrated memory system with microprocessor and analog or digital output device, a distributed memory system with microprocessor and analog or digital output device connected with digital or analog signal protocols.

Computer readable media means any source of organized information that may be processed by a computer to perform the steps developed in this invention to result in an arterial endothelial function measurement, including but not limited to: a magnetically readable storage system; optically readable storage media such as punch cards or printed matter readable by direct methods or methods of optical character recognition; other optical storage media such as a compact disc (CD), a digital versatile disc (DVD), a rewritable CD and/or DVD; electrically readable media such as programmable read only memories (PROMs), electrically erasable programmable read only memories (EEPROMs), field programmable gate arrays (FGPAs), flash random access memory (flash RAM); and remotely transmitted information by electromagnetic or optical methods.

Reactive hyperemia means an arterial response after a prolonged (typically 5 minutes) of pulse flow occlusion, followed by pulse flow resumption. Factors are released by the arterial endothelium after resumption of the blood flow causing changes in arterial diameter, smooth muscle tone (hence mechanical stress-strain properties) and wall thickness. The collection of these properties typically tend to increase pulse transit times, and decrease pulse transit speed.

Pulse transit speed means the ratio of pulse transit time divided by a known measuring distance.

Overview

Impairment of arterial endothelial function is an early event in atherosclerosis and correlates with the major risk factors for cardiovascular disease. The most widely used non-invasive measure of endothelial function involves the brachial artery (BA) diameter measurement using ultrasound imaging before and after several minutes of blood flow occlusion. The change in arterial diameter is a measure of flow-mediated vasorelaxation (FMVR). The high variability of results and high cost of instrumentation render this technique unsuitable for routine clinical use. The present invention is designed to overcome many obstacles that confine non-invasive assessment of FMVR to research settings. The invention described herein, when used in a vasorelaxive mode, is referred to as a "relaxoscope". The relaxoscope induces an artificial pulse at the superficial artery, typically via a linear actuator. An ultrasonic Doppler stethoscope detects this pulse typically between 10 and 20 cm proximal to the point of pulse induction. The delay between pulse application and detection provides the pulse transit time (PTT). By measuring PTT before and after about 5 minutes of BA occlusion and ensuing reactive hyperemia, FMVR may be measured based on the changes in PTT caused by changes in vessel caliber, smooth muscle tone and wall thickness. The results obtained are compared between the relaxoscope with M-mode BA diameter measurements in human subjects, and corresponding ultrasound measurements.

Introduction

The invention described herein uses a novel method for arterial endothelial function measurement. Endothelial dysfunction is an important initial event in atherogenesis [1, 2, 3, 4, 5] and is strongly correlated with all the major risk factors for cardiovascular disease (CVD) [6, 7, 8, 9]. In addition, it is one of the earliest predictors of CVD [6, 10] and coronary events [11]. Also, factors that are considered beneficial for cardiovascular health, such as exercise [12], appear to improve endothelial function [13]. The fact that no-assessment of endothelial function is included as part of the routine medical examination constitutes a major deficit of current clinical practice, given the extremely high incidence of CVD among the population of the Western world.

The most common method for the assessment of endothelial function is the measurement of the diameter of the brachial artery using high-resolution ultrasound before and after an arterial occlusion of several minutes duration. The reactive hyperemic flow that ensues once the occlusion is removed stimulates endothelial cells to release chemical factors that relax the surrounding vascular smooth muscle. The change in arterial caliber effected by this mechanism is termed flow-mediated vasodilation (FMD). The coefficients of variation of the FMD measurements obtained using the ultrasound imaging method varies widely from as little as 1.5% in a few studies to approximately 50% in many others [14, 15, 16, 17]. Some investigators have considered FMD values of less than 5% as indicative of endothelial dysfunction (ED), while others have observed mean FMDs of more than 5% in cardiovascular disease states. These statistics suggest that this ultrasonic imaging method of measuring FMD is too sensitive to differences in methodology to allow its routine use in a clinical setting.

Figure 1:
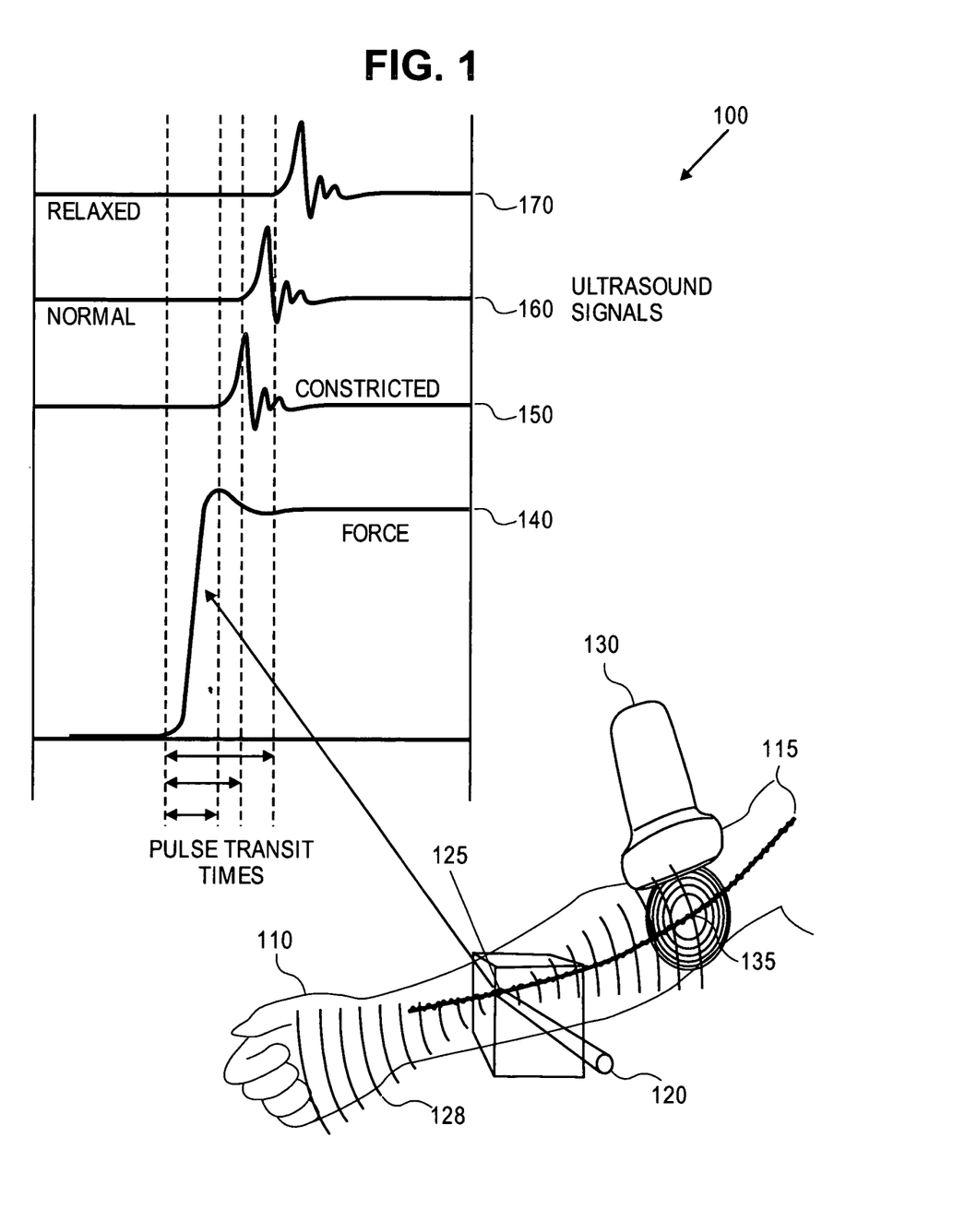
FIG. 1 is a diagrammatic representation of a brachial artery being pulsed, an ultrasonic transducer detecting the pulse, and the pulse transit time waveforms associated with constricted, normal, and relaxed arterial wave transmissions.

Disclosed herein is a new instrument, referred to as the "vascular relaxoscope", for the non-invasive assessment of flow-mediated vasorelaxation (FMVR), which theoretically provides a more sensitive measure of endothelium-mediated vasomotion than do methods that measure FMD. The relaxoscope measures vasorelaxation via the effect of this process on the transit time of an artificial pulse through a segment of an artery. FIG. 1 illustrates this schematically.

Refer now to FIG. 1, which is a diagrammatic representation of a brachial artery being pulsed, and ultrasonic transducer detecting the pulse, and the pulse transit time waveforms associated with constricted, normal, and relaxed arterial wave transmissions 100. Here a human arm 110, or other extremity having arterial structure 115 proximal to the dermal surface has a force-controlled displacement transducer 120 impinging on the skin surface, exciting a pulse in the artery 115 at a point of excitation 125. The pulse, graphically represented as waves 128 in the artery 115, propagates to a receiver 130, which senses the arrival of the pulse waveform 128 at a point 135 some distance away from the excitation point 125. Signal processing equipment (not shown here), such as a computer-controlled data acquisition system or digital oscilloscope, collects waveforms of the excitation force versus time 140, and the corresponding ultrasound detected signal for the artery 115 which is constricted 150, normal 160, and relaxed 170. These states of constriction, normality, and relaxation are further described below.

Many techniques for PTT and PWV measurement have been presented in the past [18, p. 102-106]. Most rely on calculating the time delay between the rising edges of individual natural pulse pressure or flow waves as they pass two points along the propagation path. Non-linear viscoelastic properties of arterial walls introduce acoustic dispersion: different frequency components of the pulse or flow wave travel at different speeds, temporally smearing the arrival of the impulse input waveforms. Also, pulse pressure affects transit speed. Both of these factors lead to the high variability of the measurements obtained.

Anliker et al. [19] studied the canine aorta by introducing artificial pulse waves through insertion of a vibrating device within the artery. Traveling waves were detected using an intra-arterial pressure transducer. Measurements characterized by greater accuracy and repeatability than those derived from the natural pulse wave were obtained. This may be attributed to the well-defined nature, and low amplitude of the induced pulses. Landowne performed similar invasive measurements in the human forearm. An armature within a solenoid delivered mechanical pulses to the radial artery, and resultant pressure waves were measured proximal to the site of administration using an intra-arterial catheter transducer [20]. The invention described herein, alternatively termed the "relaxoscope", which we now describe, performs this measurement non-invasively.

II. Instrument Design

Figure 2A:
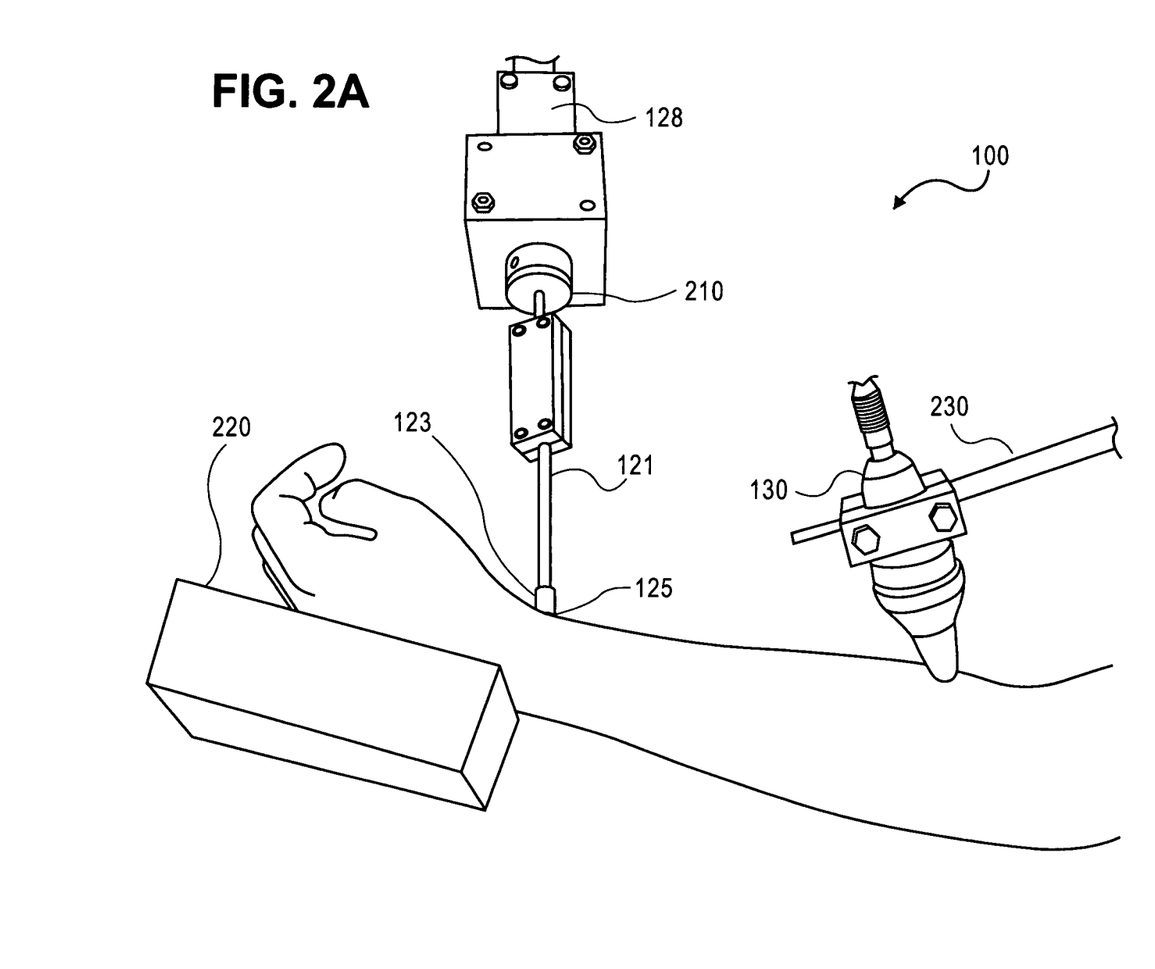
FIG. 2A is a diagram of a prototype of the invention showing the relative sizes and typical layout of one embodiment of the arterial endothelial function measurement device described herein.
Figure 2B:
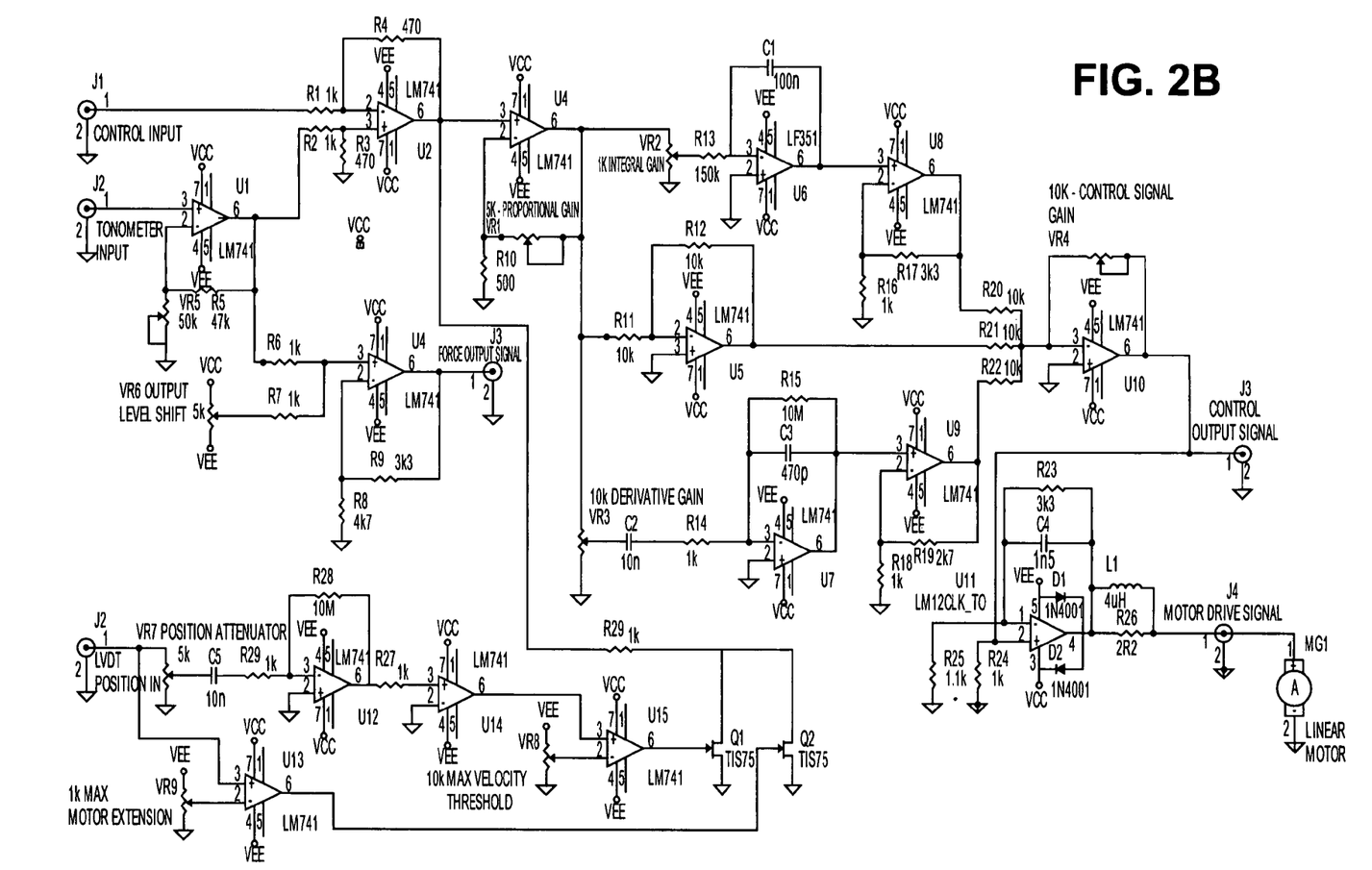
FIG. 2B is a schematic of the force- and rate-limited proportional-integral-differential (PID) motor controller electronics.

One embodiment of the invention appears in FIG. 2. Referring now to FIGS. 1, 2A and 2B, the instrument employs a force-feedback controlled linear motor (Baldor Electric Co., Fort Smith, Ark.), the actuating stem 121 of which makes contact with the skin contact 125 to introduce an artificial pulse at the superficial segment of the radial artery. An applanation tonometer 123 (Millar Instruments Inc., Houston, Tex.) is located at the free end of the stem. The applanation tonometer 123 senses the amount of applied force generated by the linear motor 210 driving the stem 121. This allows for closed-loop control of the force waveform and accommodates different lateral positions of the wrist of the subject. An analog PID controller is employed for this purpose as shown in FIG. 2B. Distance movement of the stem 121 is in turn measured by a linearly variable differential transducer (LVDT) 128.

Several centimeters proximal to the site of pulse introduction, an 8 MHz continuous wave Doppler ultrasonic stethoscope 130 records the incident flow waves produced by these pulses. Positioning of the Doppler ultrasonic stethoscope 130 is readily achieved by a many-degree-of-freedom clamping system 230. The arterial pulse transit time (PTT) is measured by the ultrasonic stethoscope 130. The pulse wave velocity (PWV) is estimated by dividing the distance between the actuator (in this case the applanation tonometer 123) and the ultrasonic sensor, by the pulse transit time. PTT measurements are preferably taken during diastole when interference between natural and induced pulses is least significant.

By applying a constant force input signal, the relaxoscope can conveniently be used to acquire the pulse pressure waveform of the subject, as previously depicted as constricted 150, normal 160, and relaxed 170 waveforms of FIG. 1.

The relaxoscope includes actuator rate limiting as a safety feature. Actuator position is measured using a linear variable differential transformer mounted on the motor armature. An analog differentiator and comparator limit the maximum speed of the armature as found in FIG. 2B.

The force input, motor control, ultrasound audio, force applied and position signals are simultaneously recorded using a multifunction data acquisition card (NI-PCI 6035E, National Instruments Corp, Austin, Tex.) at a sampling rate of 10 kHz per channel.

At present, PTT measurements are obtained manually by marking the rising edge of the induced force pulse (applied at point 125 in FIG. 2A) and the first flow signal corresponding to the arrival of the artificial pulse at the ultrasonic transducer 130. A typical set of acquired waveforms is shown in FIG. 3.

Figure 3:
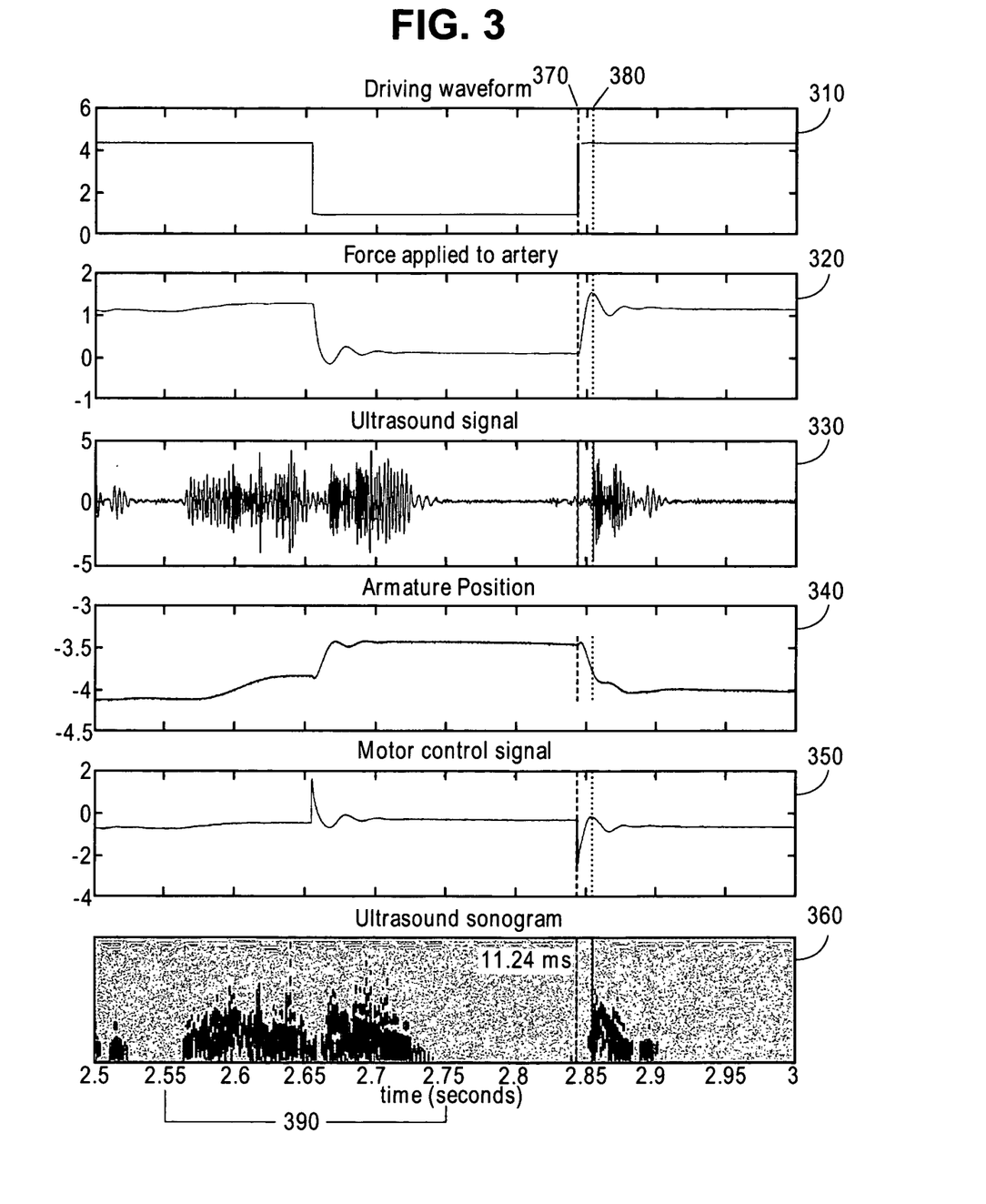
FIG. 3 is a recording of six waveforms from the invention that are plotted versus time during instrument operation: the force control input, the motor control signal, the force applied to the artery under test, the armature tip displacement, the Doppler ultrasound signal, and a sonogram of the ultrasound-signal induced changes in pulse transit time.

Refer now to FIG. 3. The five recorded waveforms from the relaxoscope are plotted here versus time. The top plot 310 shows the force control input, which is a 3 Hz square-wave. A controller produces a control signal, which is amplified and feed to the motor as waveform 350, so that the force applied to the radial artery 320 tracks the control input. Displacement of the armature tip is displayed in plot 340. As soon as the force waveform rises, the actuator tip is exerting pressure on the artery. The induced pulse travels through the artery, and the rising (earliest arriving) signal (shown at time marker 370) is shown of the Doppler ultrasound signal at the stethoscope 330. The rising edge of the force pulse 370 and that of the ultrasound signal 380 are marked as indicated, and a delay of 11.24 ms is calculated.

Note that the natural pulse signal occurs between 2.55 and 2.75 seconds at 390. It is coincident with the artificial pulse that was induced as the actuator withdrew on the previous cycle of the control input waveform. The final plot 360 is a sonogram of the ultrasound-signal induced changes in PTT (assumed to correlate with flow-mediated vasorelaxation and hence FMD), which is compared to results obtained using the present industry standard: measurements of pre- and posthyperemic arterial diameter variation derived from B-mode images and/or M-mode arterial wall echo-tracking data. The evaluation protocol consists of two procedures: Procedure A involves evaluation of flow-mediated vasorelaxation (FMVR) in the left arm of subjects, while Procedure B consists of a standard FMD assessment in the right arm. Both procedures utilize a 5-minute occlusion of the brachial artery in order to induce reactive hyperemia. The two procedures are carried out sequentially in random order on the same individual. Procedures A and B are performed with a maximum interval of one hour between the procedures.

In an alternative embodiment, a custom transducer constructed by coupling an interchangeable tip that applies force directly to the patient's wrist via an in-line load cell disposed between a linear actuator and the wrist. A preferred load cell would be Entran Devices, Inc. model ELFS-T3E-10N with a 10N full-scale range and a 250 mV full scale output, whose data sheet entitled "ELFS Series Load Cells" is attached hereto and incorporated by reference herein. Presently, a Millar Instruments SPT-310 tonometer is used for force measurement.

Further alternatives to the ultrasonic detector are readily apparent. Currently, continuous wave (CW) ultrasound is used for pulsed waveform detection. CW has no depth or flow direction discrimination, so all flow signals are added together. An improved method uses a dedicated system that allows the operator initially to locate the artery using CW and then either manually or automatically adjust the receiver depth. In this depth-resolved system, flow resolved to a depth increment of about 1 mm would be recorded and all other flow rejected. This technique reduces vibration and motion artifacts, and furthermore excludes venous flow. It also increases the resolution of the rising edge of the received ultrasound signal by restricting the spatial sampling of flow. Yet another benefit is that, since the induced arterial pulses typically travel in the opposite direction to normal (non-reflected) arterial pulses, natural pulses are very low level, and hence hardly noticeable in the detected signal, which makes for a significant increase in the signal-to-noise ratio.

In the present embodiment, there are two alternative ultrasonic transducers used. The first is an 8 MHz continuous wave probe, which has no depth or direction discrimination. The second ultrasonic transducer is a linear ultrasonic imaging probe running at selectable 7.5 MHz and 10 MHz frequencies. The second ultrasonic transducer is further attached to an Esaote AU5 imager in PW mode. With this equipment configuration, flow direction and depth may be resolved, resulting in a much cleaner, higher signal to noise ratio signal under most circumstances.

A Tektronics TDS200 oscilloscope is typically used to view the quality of the force and ultrasound signals in real time. The latter signal comes directly from the ultrasonic flow meter, which outputs an audio signal. When both forward and reverse flow audio signals are available separately (when PW is used), the reverse signal is connected to the oscilloscope.

All signals are recorded by a National Instruments PCI-6035E multifunction data acquisition board in communication with a computer data acquisition system. The following signals are sampled at 10 kHz each with this arrangement:
1. the position of the LVDT;
2. the applied force derived from the tonometer output amplified by a strain gauge bridge amplifier;
3. the motor control signal;
4. the ultrasound flow meter audio signal; and
5. the driving waveform.

A specific clinical protocol is executed automatically by a software script on the computer system. The script verbally informs the operator of when recording is occurring and the progress of the protocol, including time elapsed. A variety of instructions for protocols such as "Inflate cuff", "Deflate cuff", "Take nitroglycerin", "Inhale albuterol" are also given verbally.

III. Evaluation of Arterial Endothelial Function

To determine how vasorelaxation can be measured via PTT, we refer to the Moens-Korteweg equation, which describes with reasonable accuracy the relationship between PWV and arterial dimensions and material properties:

$$\frac{1}{PTT} = c = \sqrt{\frac{Eh}{2\rho R}}$$

where c is the PWV, E is the Young's modulus of the arterial wall, h is the wall thickness, $\rho$ is the blood density and R represents the arterial radius [21, p. 91]. As R increases owing to endothelium-mediated smooth muscle relaxation, the PWV decreases. Also, relaxation of vascular smooth muscle reduces E and the wall thickness h, and hence c [18, p. 100-101]. Thus, the greater the drop in PWV between preocclusion and postocclusion measurements, the more robust the endothelium-mediated dilation response will be.

IV. Preliminary Evaluation of the Relaxoscope in Human Subjects

The relaxoscope is currently undergoing a preliminary evaluation in which measurements of reactive hyperemia-induced changes in PTT (assumed to correlate with flow-mediated vasorelaxation and hence FMD) are compared to results obtained using the present industry standard: measurements of pre- and posthyperemic arterial diameter variation derived from B-mode images and/or M-mode arterial wall echo-tracking data. The evaluation protocol consists of two procedures. Procedure A involves evaluation of flow-mediated vasorelaxation (FMVR) in the left arm of subjects, while Procedure B consists of a standard FMD assessment in the right arm. Both procedures utilize a 5 minute occlusion of the brachial artery in order to induce reactive hyperemia.

The two procedures are carried out sequentially in random order on the same individual. Procedures A and B are performed with a maximum interval of one hour between the procedures.

Procedure B employs an M-mode wall echo-tracking diameter measurement system (Wall Track System 11, Pie Medical, Maastricht, Netherlands).

V. Results

Figure 4:
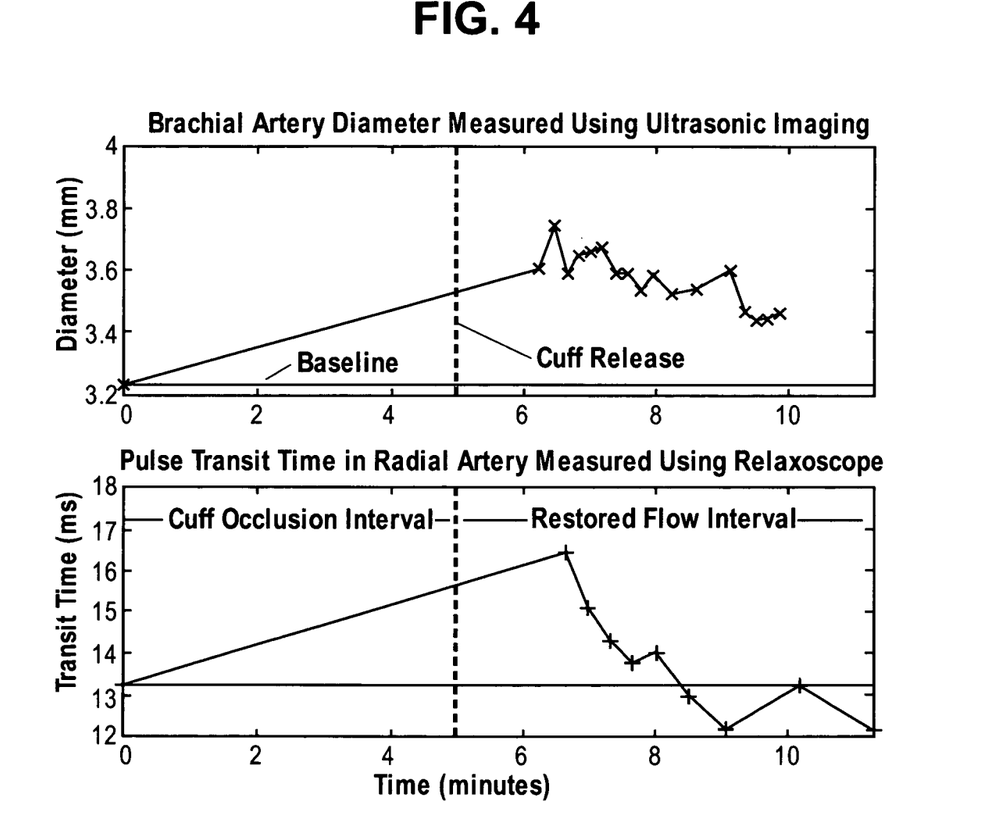
FIG. 4 indicates data obtained from a 30 year old male, with the upper plot displaying ultrasonic probe measured diameter versus time in minutes of the brachial artery, while the lower plot follows the same experimental sequence, but measured pulse transit time (PTT) versus time in minutes for the same individual's radial artery.

The results of a single study appear in FIG. 4. These data were obtained from a 30-year-old male. In FIG. 4 the upper plot displays ultrasonic probe measured diameter versus time in minutes of the brachial artery, while the lower plot follows the same experimental sequence, but displays measured pulse transit time (PTT) versus time in minutes for the same individual's radial artery.

Figure 5:
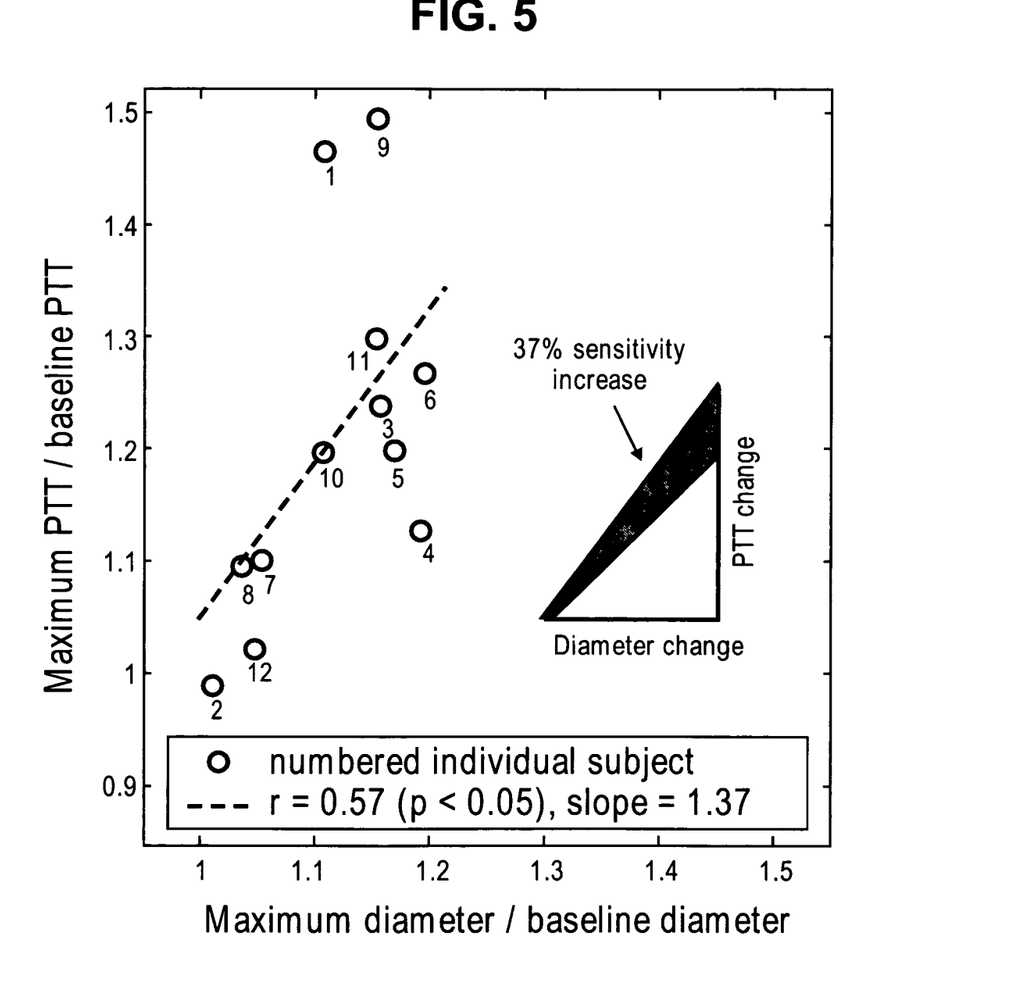
FIG. 5 illustrates the maximum fractional changes in diameter versus change in pulse transit time (PTT) for eleven subjects showing a correlation between these two quantities is 0.56 (p<0.05).

Similar response time courses have been observed among the eleven subjects evaluated so far in this ongoing preliminary study. FIG. 5 illustrates the maximum fractional changes in diameter versus change in PTT for the same eleven subjects. The correlation between these two quantities is 0.56 ($p<0.05$). The relaxoscope's PTT measurements exhibit approximately 20% greater sensitivity to endothelium-mediated vasorelaxation than the diameter measurements. Restating this, the least squares linear regression of the eleven data points yields a line with a 1.21 slope, indicating an ~21% sensitivity advantage in favor of the pulse transit time measurement relative to diameter measurement.

VI. Discussion

The relaxoscope has the potential to offer a simple low cost means of non-invasive evaluation of endothelial function that is more sensitive than methods based on brachial artery diameter measurements.

The current human subject evaluation protocol is insufficient to decisively demonstrate the performance of the relaxoscope. It is especially difficult to evaluate the sensitivity of the relaxoscope to FMVR through comparison with brachial artery diameter measurement owing to the high variability of the latter technique and the unknown variability of the relaxoscope PTT estimate. A protocol involving the administration of agents such as sodium nitroprusside or nitroglycerin that are known to relax arterial walls would be a more effective approach. However, among the five young subjects examined so far under the present protocol, all exhibited increased posthyperemic PTT. This is suggestive of intact endothelial function typical of individuals with no cardiovascular risk factors in this age group. Repeatability studies are required to reinforce these observations, but they are consistent with the underlying physics of vasorelaxation.

In contrast to ultrasonic imaging methods, the relaxoscope does not require precise transducer positioning and the attendant skills of an experienced ultrasound technician. This greater ease of use reduces the significant measurement error that is easily introduced into FMD measurements by slight movements of the subject under examination. It is thought that the relaxoscope may potentially be manufactured for as low as $5,000US, or approximately one fifteenth of the cost of an ultrasonic imager.

REFERENCES

[1] D. S. Celermajer, K. E. Sorensen, V M. Gooch, D. J. Spiegelhalter, 0.1. Miller, L. D. Sullivan, J. K. Lloyd, and J.

E. Deanfield, "Non-invasive detection of endothelial dysfunction in children and adults at risk of atherosclerosis," The Lancet, vol. 340, pp. 1111-1115, November 1992.

[2] H. Yasue, K. Matsuyama, K. Matsuyama, K. Okumura, Y Morikami, and H. Ogawa, "Responses of angiographically normal human coronary arteries to intracoronary injection of acetylcholine by age and segment: Possible role of early atherosclerosis," Circulation, vol. 81, pp. 482-490, 1990.

[3] A. Zeiher, H. Drexler, H. Wollschäger, and H. Just, "Modulation of coronary vasodilator tone in humans: Progressive endothelial dysfunction with different early stages of coronary atherosclerosis," Circulation, vol. 83, pp. 391 401, 1991.

[4] J. McLenachan, J. Vita, R. Fish, C. Treasure, D. Cox, P. Ganz, and A. P. Selwyn, "Early evidence of endothelial vasodilator dysfunction at coronary branch points," Circulation, vol. 82, pp. 1169-1173, 1990.

[5] D. A. Cox, J. A. Vita, C. B. Treasure, R. D. Fish, R. W. Alexander, P. Ganz, and A. P. Selwyn, "Atherosclerosis impairs flow-mediated dilation of coronary arteries in humans," Circulation, vol. 80, pp. 45"65, September 1989.

[6] J. Vita, C. Treasure, G. Nabel, J. McLenachan, R. Fish, A. Yeung, V Vekshtein, A. Selwyn, and E Ganz, "The coronary vasodilator response to acetylcholine relates to risk factors for coronary artery disease," Circulation, vol. 81, pp. 491-497, 1990.

[7] R. Ross, "The pathogenesis of atherosclerosis: a perspective for the 1990s," Nature, vol. 362, pp. 801-9, 1993.

[8] K. E. Sorensen, D. S. Celermajer, D. Geogakopoulos, G. Hatcher, D. J. Betteridge, and J. E. Deanfield, "Impairment of endothelium-dependent dilation is an early event in children with familial hypercholesterolemia and is related to the lipoprotein (a) level," Journal of Clinical Investigation, vol. 93, pp. 50-55, January 1994.

[9] M. Williams, W. Sutherland, M. McCormick, S. de Jong, and R. Walker, "Impaired endothelial function following a meal rich in used cooking fat," Journal of the American College of Cardiology, vol. 33, pp. 1050-5, March 1999.

[10] D. Celermajer, K. Sorensen, C. Bull, J. Robinson, and J. Deanfield, "Endothelium-dependent dilation in the systemic arteries of asymptomatic subjects relates to coronary risk factors and their interaction," Journal of the American College of Cardiology, vol. 24, pp. 1468-74, November 1994.

[11] T. Neunteufl S. Heher, R. Katzenschlager, G. Wolft K. Kostner, G. Maurer, and E Weidinger, "Late prognostic value of flow-mediated dilation in the brachial artery of patients with chest pain," American Journal of Cardiology, vol. 86, no. 2, pp. 207-10, 2000.

[12] R. M. Krauss, R. H. Eckel, B. Howard, L. J. Appel, S. R. Daniels, R. J. Deckelbaum, J. W. Erdman, E Kris-Etherton, 1. J. Goldberg, T. A. Kotchen, A. H. Lichtenstein, W. E. Mitch, R. Mullis, K. Robinson, J. Wylie-Rosett, S. S. Jeor, J. Suttie, D. L. Tribble, and T. L. Bazzarre, "AHA dietary guidelines: revision 2000: A statement for healthcare professionals from the nutrition committee of the American Heart Association," Circulation, vol. 102, pp. 2284-2299, October 2000.

[13] Y Higashi, S. Sasaki, S. Kurisu, A. Yoshimizu, N. Sasaki, H. Matsuura, G. Kajiyama, and T. Oshima, "Regular aerobic exercise augments endothelium-dependent vascular relaxation in normotensive as well as hypertensive subjects: role of endothelium-derived nitric oxide," Circulation, vol. 100, pp. 1194-1202, September 1999.

[14] K. E. Sorensen, D. S. Celermajer, D. J. Spiegelhalter, D. Georgakopoulos, J. Robinson, O. Thomas, and J. E. Deanfield, "Non-invasive measurement of human endothelium dependent arterial responses: accuracy and reproducibility," Br Heart J, vol. 74, pp. 247-253, September 1995.

[15] T. C. Andrews, E. J. Whitney, G. Green, R. Kalenian, and B. E. Personius, "Effect of gemfibrozil+/−niacin+/−cholestyramine on endothelial function in patients with serum low-density lipoprotein cholesterol levels <160 mg/dl and high-density lipoprotein cholesterol levels G40 mg/dl," Am J Cardiol, vol. 80, pp. 831-835, October 1997.

[16] K. L. Hardie, S. Kinlay, D. B. Hardy, J. Wlodarczyk, J. S. Silberberg, and P. J. Fletcher, "Reproducibility of brachial ultrasonography and flow-mediated dilatation (FMD) for assessing endothelial function," Aust N Z J Med, vol. 27, pp. 649-652, December 1997.

[17] N. M. de Roos, M. L. Bots, and M. B. Katan, "Replacement of dietary saturated fatty acids by trans fatty acids lowers serum HDL cholesterol and impairs endothelial function in healthy men and women," Atherosclerosis, thrombosis and vascular biology, vol. 21, pp. 1233-1237, 2001.

[18] W. Nichols and M. O'Rourke, McDonald's blood flow in arteries, 4th ed. Edward Arnold, 1998.

[19] M. Anliker, M. B. Histand, and E. Ogden, "Dispersion and attenuation of small artificial pressure waves in the canine aorta," Circulation Research, vol. 23, pp. 539-551, October 1968.

[20] M. Landowne, "A method using induced waves to study pressure propagation in human arteries," Circulation Research, vol. 5, pp. 594-601, November 1957.

[21] U. Dinnar, Cardiovascular Fluid Dynamics. CRC Press, 1981.

CONCLUSIONS

All publications, patents, and patent applications mentioned in this specification are herein incorporated by reference to the same extent as if each individual publication or patent application were each specifically and individually indicated to be incorporated by reference.

The description given here, and best modes of operation of the invention, are not intended to limit the scope of the invention. Many modifications, alternative constructions, and equivalents may be employed without departing from the scope and spirit of the invention.

We claim:

1. A method of arterial endothelial function measurement, the method comprising:
   a) imparting a first set of one or more artificial pulses into an artery endothelium using an actuator, said artery endothelium having an initial pulse transit speed;
   b) detecting the arrival of at least one of the one or more artificial pulses at a detector to determine the initial pulse transit speed;
   c) modifying the artificial pulse transit speed of said artery endothelium;
   d) imparting a second set of one or more artificial pulses using an actuator into said artery endothelium;
   e) detecting the arrival of at least one of the one or more artificial pulses with said detector to form a modified pulse transit speed;
   f) calculating a difference between said modified pulse transit speed and said initial pulse transit speed; and
   g) calculating a ratio between said modified pulse transit speed and said initial pulse transit speed, wherein said ratio is a measurement of arterial endothelial function.

2. The method of claim 1 wherein said detecting steps take place with said detector at substantially the same distance from where said pulses are imparted.

3. The method of claim 1 wherein said detecting steps take place with said detector at different distances from where said pulses are imparted.

4. The method of claim 1 further comprising:
 a) outputting as a signal output one or more signals selected from the group consisting of:
  i) the initial pulse transit speed,
  ii) the modified pulse transit speed,
  iii) a difference of pulse transit speeds, formed by calculating a difference between said modified pulse transit speed and said initial pulse transit speed, and
  iv) a ratio of pulse transit speeds formed by dividing said modified pulse transit speed with said initial pulse transit speed.

5. The method of claim 1 wherein said modifying step is accomplished by relaxing said artery with one or more of the group consisting of:
 electrostimulation, reactive hyperemia, applying vasorelaxant sodium nitroprusside, nitroglycerin, albuterol, salbutamol, nicotine, and carbon dioxide.

6. The method of claim 1 wherein said detector in said detecting step is a high frequency Doppler ultrasonic stethoscope, a pulsed wave flow measurement device, an ultrasonic imager, electromagnetic detector, an optical detector, a force sensor, a microphone, or a nuclear magnetic resonance imager.

7. The method of claim 1 wherein said first and second sets of artificial pulses in said imparting steps are effected by a force-displacement controlled linear actuator.

8. The method of claim 7 wherein said modifying step is accomplished by constricting said artery with one or more of the group consisting of: electrostimulation, L-NAME, L-NMMA, nicotine, nitric oxide synthase inhibitors, carbon dioxide, epinephrine, and norepinephrine.

9. An article of manufacture for arterial endothelial function measurement using a computer, said article comprising: a non-transitory computer readable medium comprising instructions for said computer to execute or control a set of steps comprising the steps of claim 1.

10. The article of manufacture for arterial endothelial function measurement of claim 9 further comprising: (a) an actuator to create one or more artificial pulses in an artery endothelium; (b) a detector of said pulses in said artery endothelium; (c) a signal output of a differential pulse transit time, said differential the difference between pulse transit time before and after modification of pulse transit time, and (d) means for connecting the computer to said actuator, detector and signal output.

* * * * *